(12) United States Patent
Choi et al.

(10) Patent No.: US 12,097,076 B2
(45) Date of Patent: Sep. 24, 2024

(54) METHOD AND DEVICE FOR DISPLAYING PASSIVE CAVITATION IMAGE

(71) Applicant: Min Joo Choi, Jeju-si (KR)

(72) Inventors: Min Joo Choi, Jeju-si (KR); Mok Kun Jeong, Seoul (KR); Sung Jae Kwon, Seoul (KR)

(73) Assignee: Min Joo Choi, Jeju-si (KR)

( * ) Notice: Subject to any disclaimer, the term of this patent is extended or adjusted under 35 U.S.C. 154(b) by 313 days.

(21) Appl. No.: 17/426,190

(22) PCT Filed: Jan. 3, 2020

(86) PCT No.: PCT/KR2020/000144
§ 371 (c)(1),
(2) Date: Jul. 28, 2021

(87) PCT Pub. No.: WO2020/159090
PCT Pub. Date: Aug. 6, 2020

(65) Prior Publication Data
US 2022/0101579 A1 Mar. 31, 2022

(30) Foreign Application Priority Data
Jan. 29, 2019 (KR) .................. 10-2019-0011463

(51) Int. Cl.
*A61B 8/08* (2006.01)
*A61B 8/00* (2006.01)
(Continued)

(52) U.S. Cl.
CPC ........ *A61B 8/5246* (2013.01); *G01S 7/52047* (2013.01); *A61B 8/463* (2013.01);
(Continued)

(58) Field of Classification Search
CPC ..... A61B 8/5246; A61B 8/463; A61B 8/5207; A61B 2017/22008; A61B 8/483;
(Continued)

(56) References Cited

U.S. PATENT DOCUMENTS

| 9,017,261 B2 | 4/2015 | Watanabe |
| 2012/0130288 A1 | 5/2012 | Holland et al. |
| 2019/0009108 A1 | 1/2019 | Lee et al. |

FOREIGN PATENT DOCUMENTS

| KR | 1020070019070 A | 2/2007 |
| KR | 101552427 B1 | 9/2015 |
| KR | 101643304 B1 | 7/2016 |

OTHER PUBLICATIONS

NPL2 "2D and 3D real-time passive cavitation imaging of pulsed cavitation ultrasound therapy in moving tissues" Daniel Suarez Escudero et al 2018 Phys. Med. Biol. 63 235028 (Year: 2018).*
(Continued)

*Primary Examiner* — Luke D Ratcliffe
*Assistant Examiner* — Sanjida Naser
(74) *Attorney, Agent, or Firm* — Rabin & Berdo, P.C.

(57) ABSTRACT

A method for displaying a passive cavitation image that shows characteristic information of a passive cavitation includes: receiving an ultrasound signal caused by the passive cavitation; generating a plurality of first passive cavitation images for the passive cavitation at predetermined respective time frame using the received ultrasound signal by a DAS beam forming; generating a plurality of second passive cavitation images in which a maximum magnitude signal region is displayed by selecting a main lobe region having a magnitude greater than or equal to a predetermined value in the respective first passive cavitation image; generating a main lobe passive cavitation image in which a main region is displayed in the respective time frame by superimposing the plurality of the second passive cavitation (Continued)

images obtained for the respective time frame; and generating a passive cavitation image by displaying the main lobe passive cavitation image on a background image.

14 Claims, 9 Drawing Sheets

(51) Int. Cl.
    *A61B 17/22*     (2006.01)
    *A61N 7/02*     (2006.01)
    *G01S 7/52*     (2006.01)

(52) U.S. Cl.
    CPC ... *A61B 8/5207* (2013.01); *A61B 2017/22008* (2013.01); *A61N 7/02* (2013.01); *G01S 7/52074* (2013.01)

(58) Field of Classification Search
    CPC ...... A61B 2017/22007; A61B 17/2256; G01S 7/52047; G01S 7/52074; G01S 7/52036; G01S 15/8913; G01S 15/8915; A61N 7/02; A61N 2007/0039; A61N 2007/0052; A61N 2007/0095; A61N 7/00; G01H 17/00; G06T 3/40; G06T 7/00; G06T 7/90; G06T 2207/10132
    See application file for complete search history.

(56) References Cited

OTHER PUBLICATIONS

NPL1 "Power cavitation-guided blood-brain barrier opening with focused ultrasound and microbubbles" M T Burgess et al. 2018 Phys. Med. Biol. 63 065009 (Year: 2018).*

* cited by examiner

[FIG. 1]
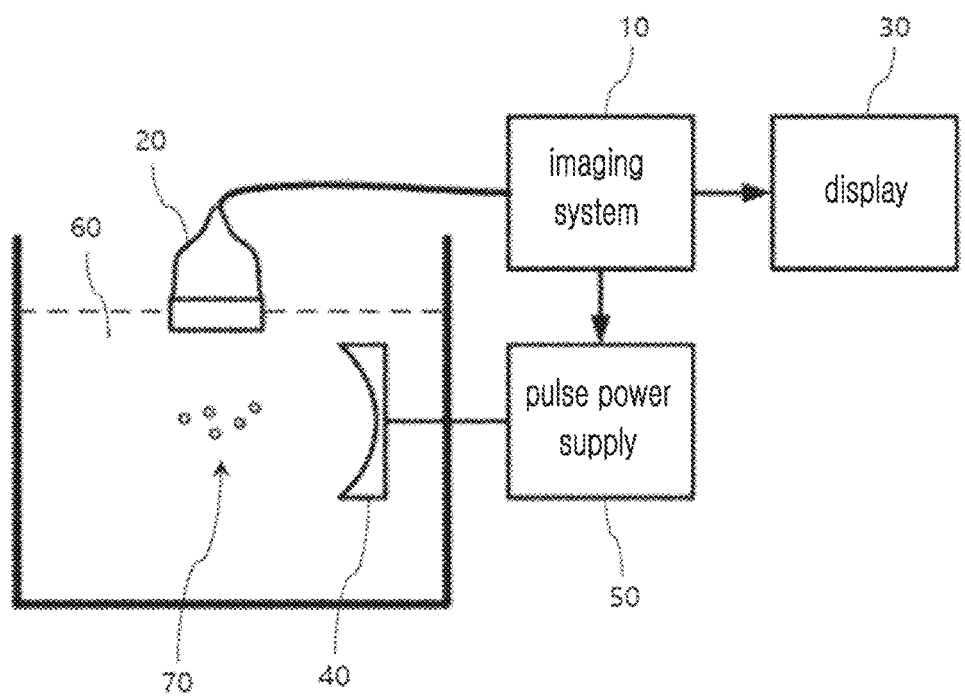

[FIG. 2]
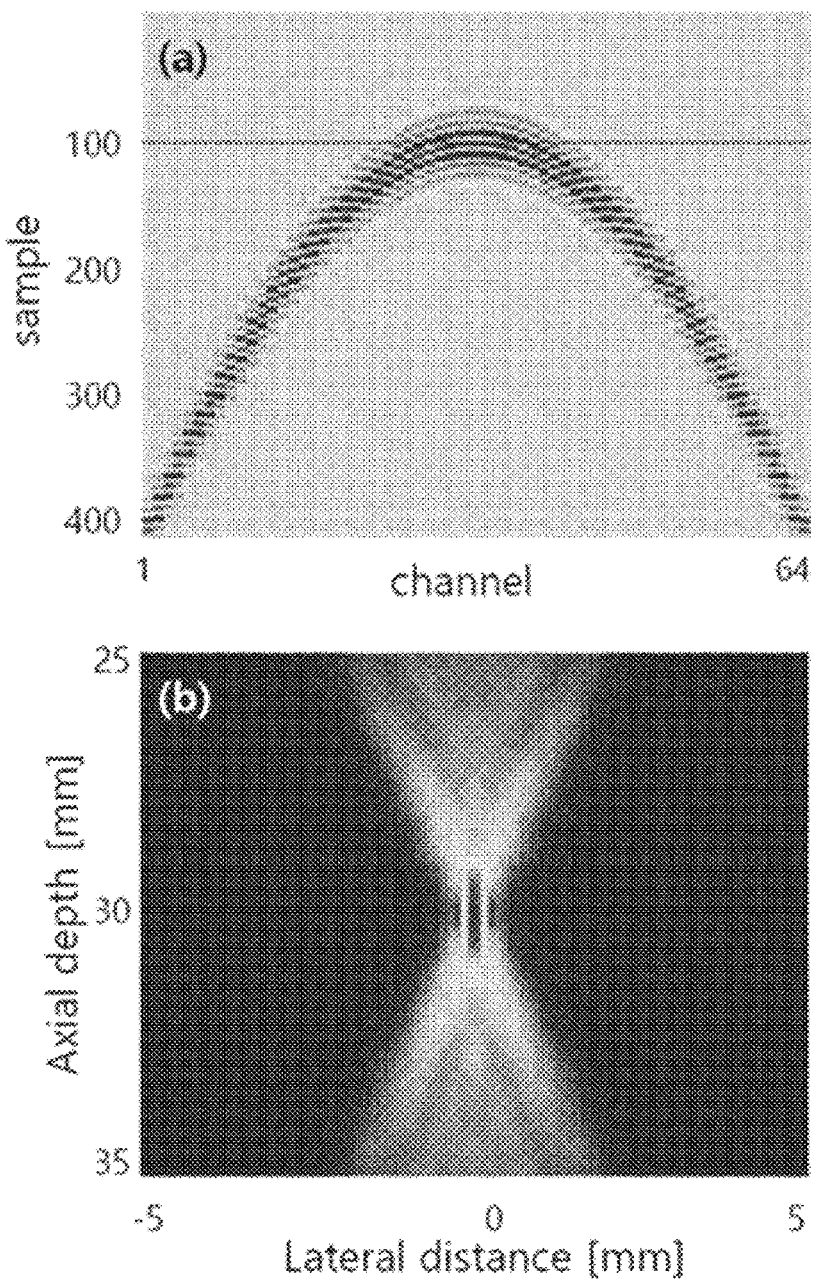

[FIG. 3]
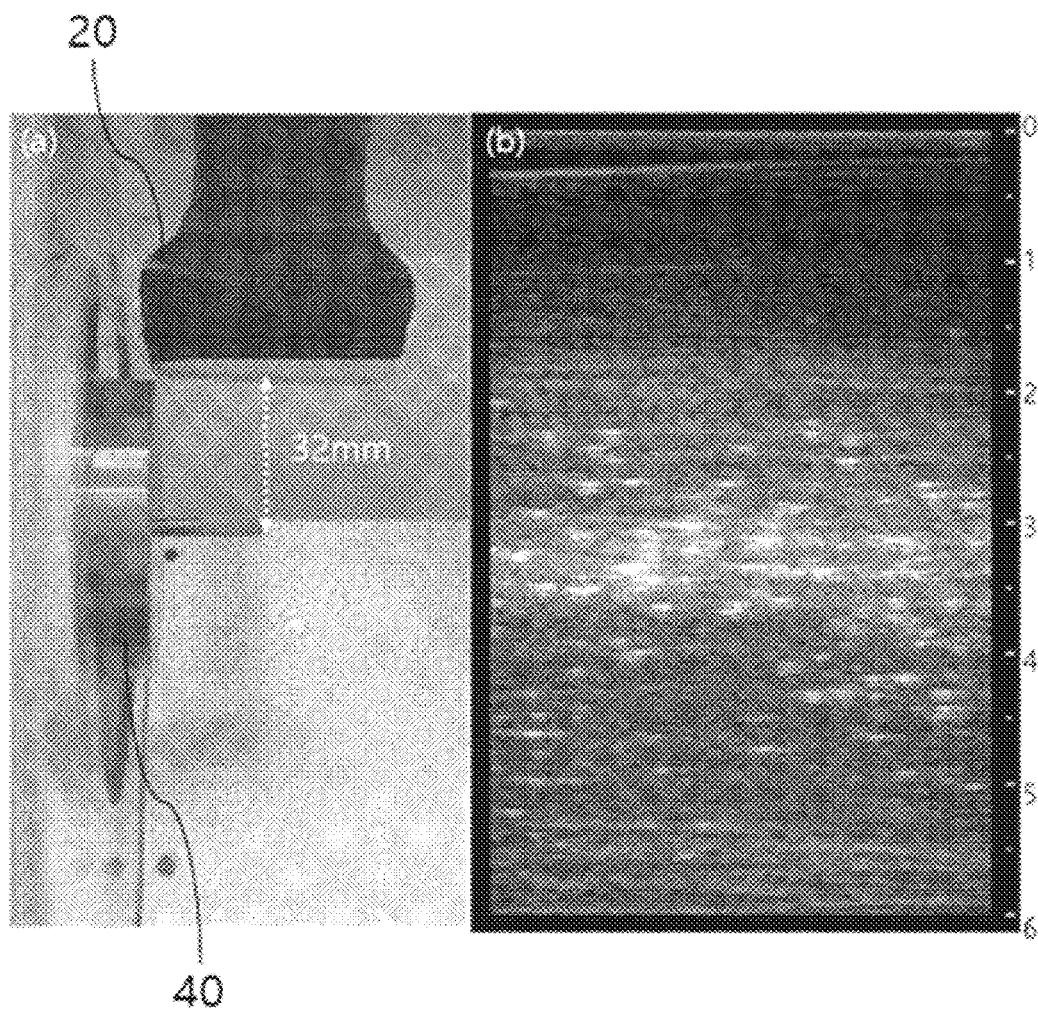

[FIG. 4]
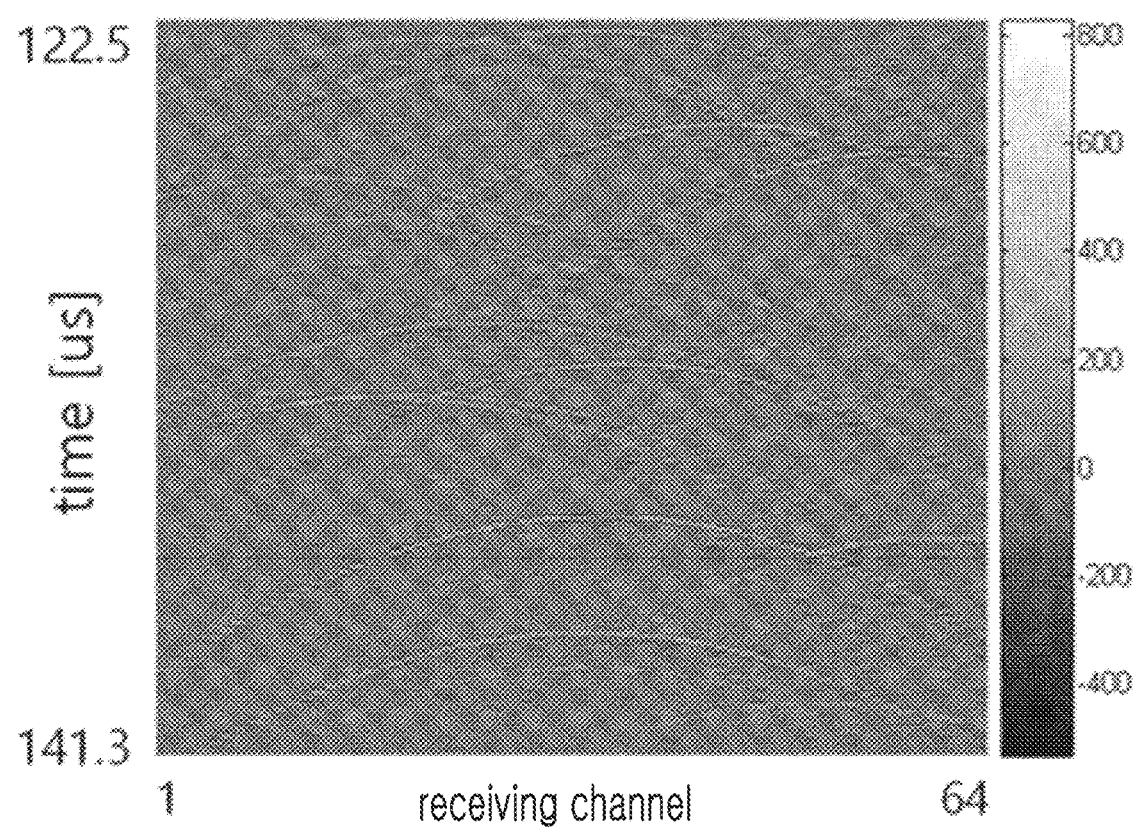

[FIG. 5]
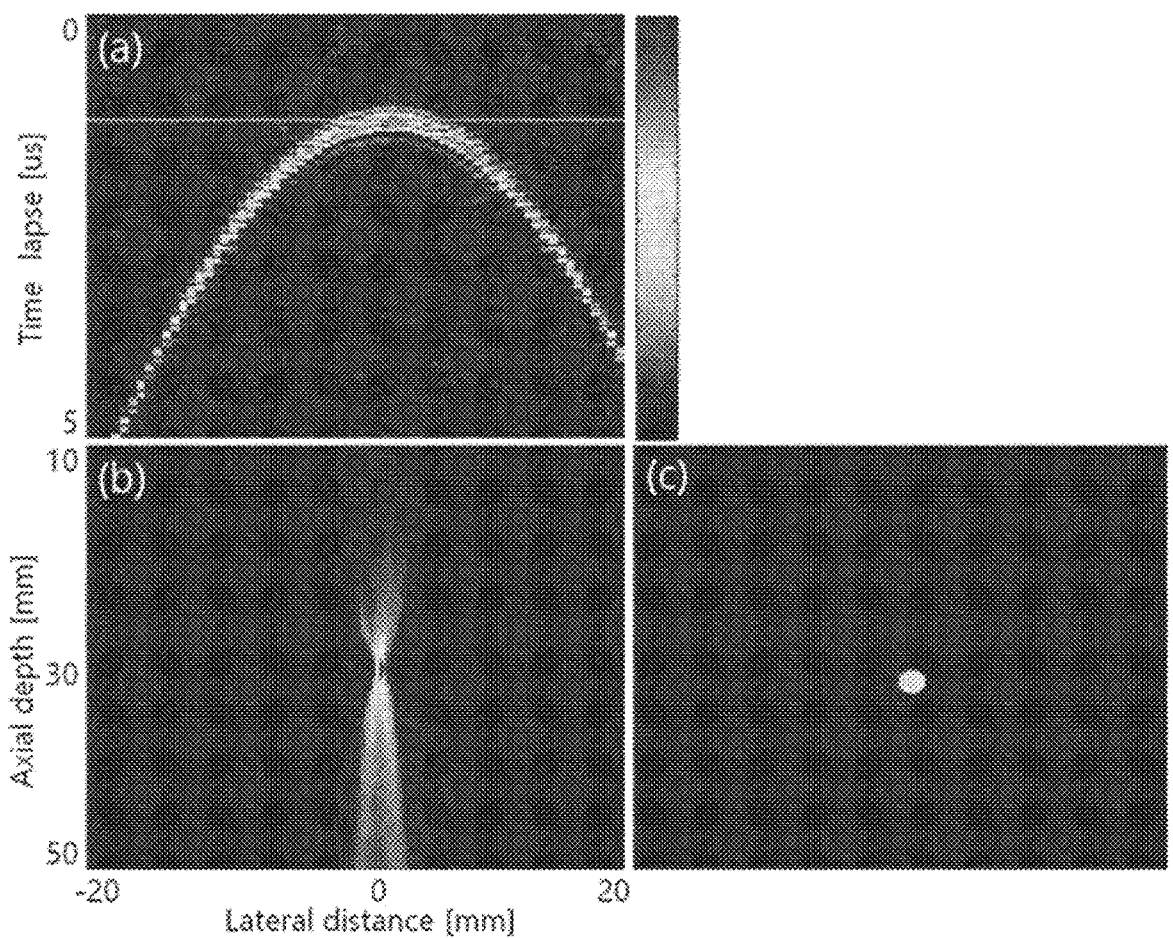

[FIG. 6]
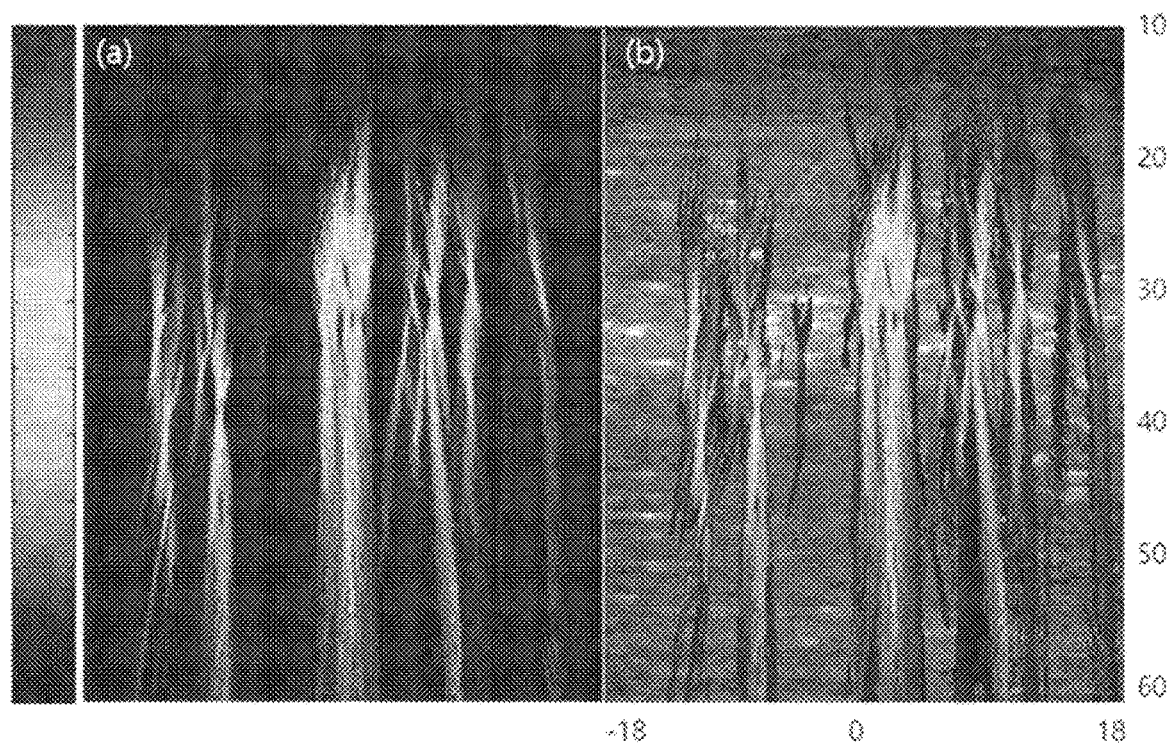

[FIG. 7]
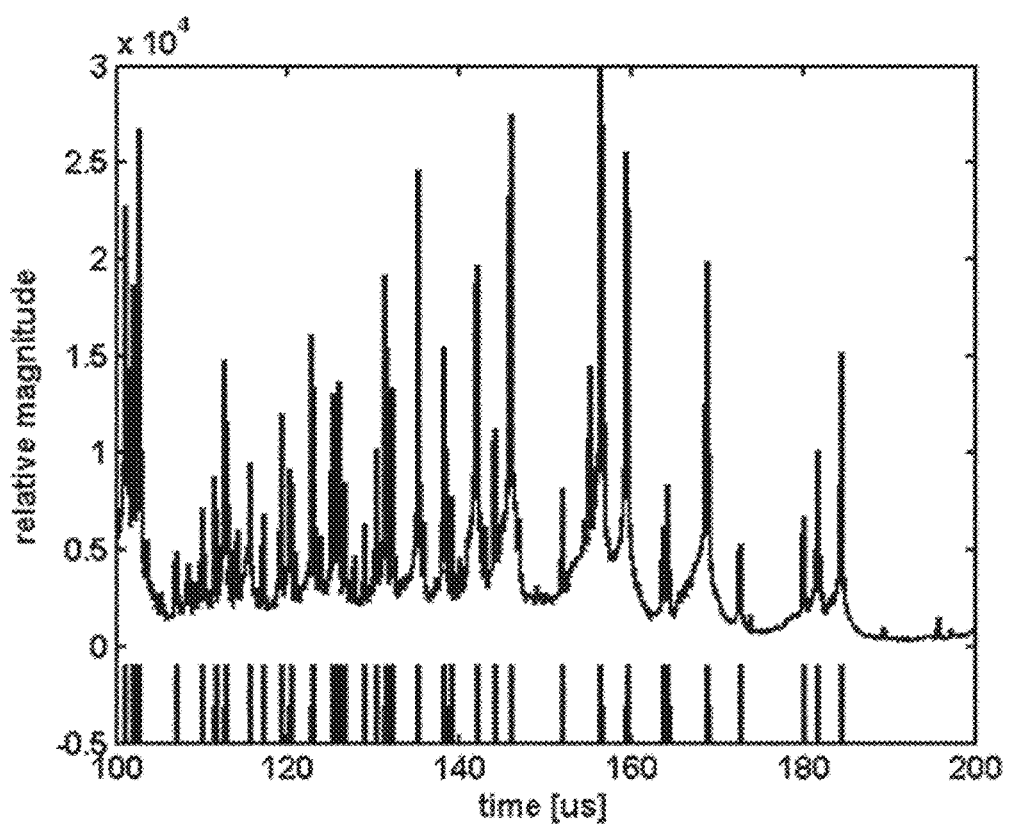

[FIG. 8]
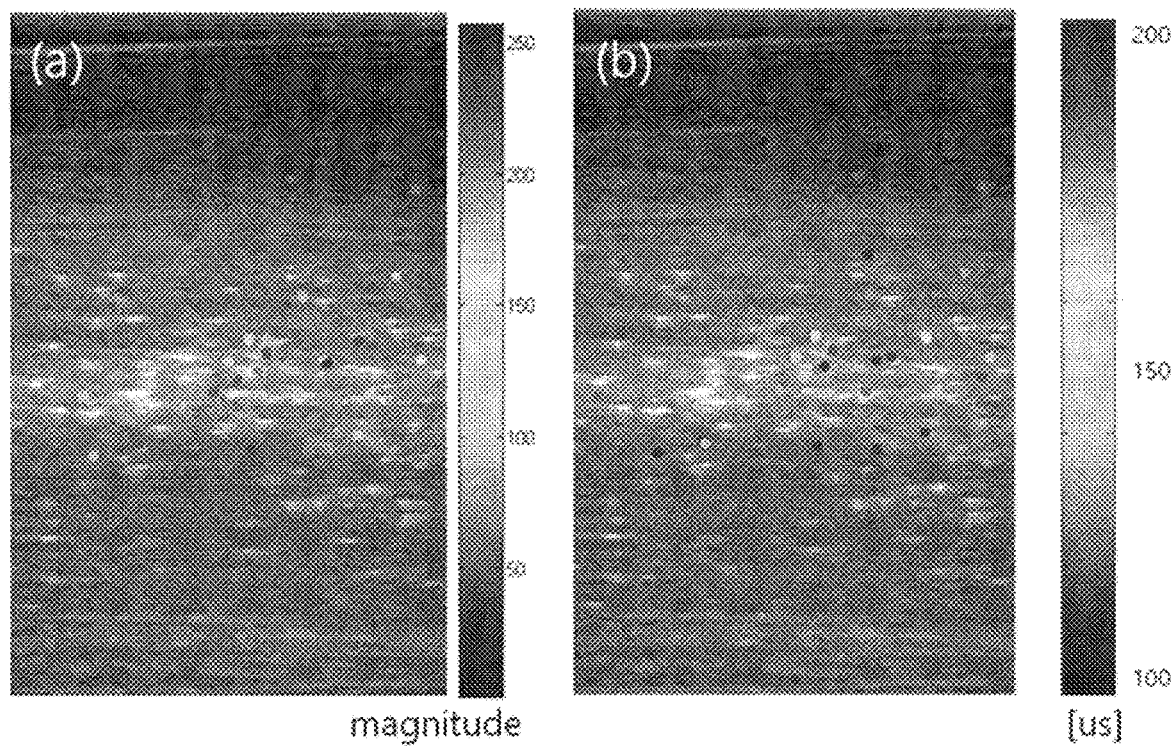

[FIG. 9]
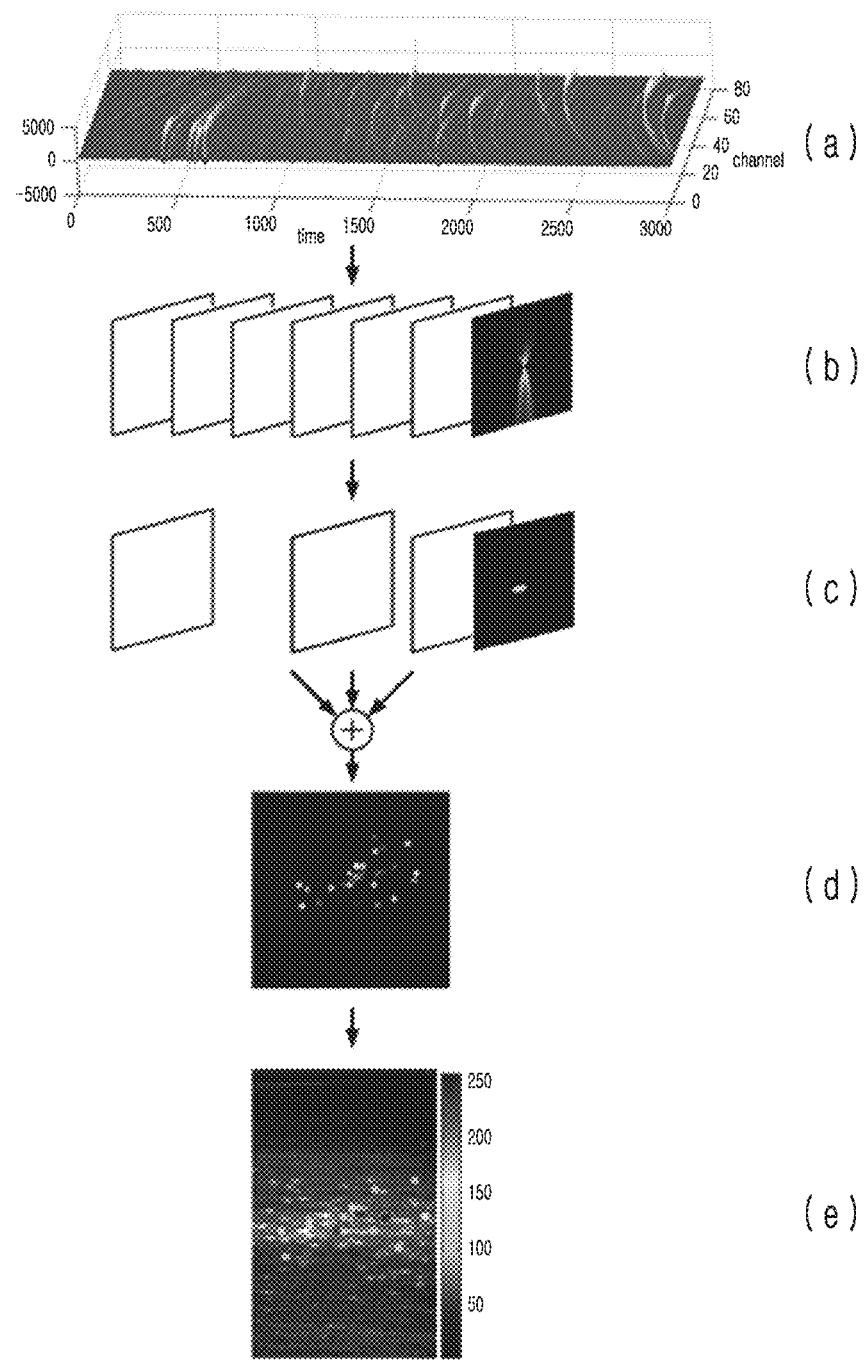

METHOD AND DEVICE FOR DISPLAYING PASSIVE CAVITATION IMAGE

CROSS-REFERENCE TO RELATED APPLICATION

This application claims the benefit of Korean Patent Application No. 10-2019-0011463 filed on Jan. 29, 2019, which is incorporated by reference herein in its entirety.

TECHNICAL FIELD

The present invention relates to a method and a device for displaying an image of passive cavitation generated by ultrasound irradiation to a medium.

BACKGROUND ART

Passive cavitation may be generated when high-power ultrasound such as high-intensity focused ultrasound or shock wave is irradiated to a medium such as a human body. Due to the characteristics of ultrasound that repeat compression and expansion, ultrasound irradiated to a medium causes pressure fluctuations, and bubbles are generated mainly by negative pressure. The bubbles generated in this way inertially rapidly contract and burst at a certain point to cause a so-called passive ultrasound cavitation phenomenon. The ultrasound cavitation caused by the ruptures of bubbles causes secondary ultrasound or shock wave.

Since secondary ultrasound emitted in a series of processes of generation of bubbles, dynamic behavior of bubbles and inertial rupture, or the like due to such ultrasound causes various effects of ultrasound, e.g., cell destruction, stone crushing, etc., it is very important to observe and track the ultrasound signal induced by the ultrasound cavitation phenomenon.

prior art document: U.S. Pat. No. 9,017,261 (Apr. 28, 2015)

DETAILED DESCRIPTION OF THE INVENTION

Technical Problem

An object of the present invention is to provide a method for displaying images of region where passive cavitation phenomenon occurs due to ultrasound irradiated to a medium, i.e., passive cavitation image (PCI).

Technical Solution

According to an embodiment of the present invention, a method for displaying a passive cavitation image that shows characteristic information of a passive cavitation includes: receiving an ultrasound signal caused by the passive cavitation; generating a plurality of first passive cavitation images for the passive cavitation at predetermined respective time frame using the received ultrasound signal by a DAS (Delay And Sum) beam forming; generating a plurality of second passive cavitation images in which a maximum magnitude signal region is displayed by selecting a main lobe region having a magnitude greater than or equal to a predetermined value in the respective first passive cavitation image; generating a main lobe passive cavitation image in which a main region is displayed in the respective time frame by superimposing the plurality of the second passive cavitation images obtained for the respective time frame; and generating a passive cavitation image by displaying the main lobe passive cavitation image on a background image.

The second passive cavitation image may include an information on a signal magnitude of the maximum magnitude signal region.

The information on the signal magnitude of the maximum magnitude signal region may be expressed as a color or gray scale image.

The second passive cavitation image may include an information on a signal generation time of the maximum magnitude signal region.

The information on the signal generation time of the maximum magnitude signal region may be expressed as a color or gray scale image.

The second passive cavitation image may be a 3D image in which an image information on a signal magnitude of the information on the maximum magnitude signal region is shown on a time axis as a signal generation time information of the maximum magnitude signal region.

The information on the signal magnitude of the maximum magnitude signal region may be expressed as a color or gray scale image.

According to an embodiment of the present invention, a device for displaying a passive cavitation image that shows characteristic information of a passive cavitation includes: an ultrasound transducer that is configured to be able to generate ultrasound to a ultrasound transmitting medium; a pulser power supply that generates a pulse power applied to the ultrasound transducer; an imaging probe that receives an ultrasound signal caused by a passive cavitation generated by the ultrasound generated in the ultrasound transmitting medium; and an imaging system that displays the passive cavitation image using the ultrasound signal received by the imaging probe. The imaging system is configured to perform: receiving the ultrasound signal caused by the passive cavitation; generating a plurality of first passive cavitation images for the passive cavitation at predetermined respective time frame using the received ultrasound signal by a DAS (Delay And Sum) beam forming; generating a plurality of second passive cavitation images in which a maximum magnitude signal region is displayed by selecting a main lobe region having a magnitude greater than or equal to a predetermined value in the respective first passive cavitation image; generating a main lobe passive cavitation image in which a main region is displayed in the respective time frame by superimposing the plurality of the second passive cavitation images obtained for the respective time frame; and generating a passive cavitation image by displaying the main lobe passive cavitation image on a background image.

Advantageous Effects

According to an embodiment of the present invention, a complex side lobe is removed from the passive cavitation image that is obtained by spatiotemporal imaging of the intensity of the ultrasound signal emitted by the cavitation phenomenon, and the location, time and the intensity of the rupture, which are key information of the ultrasound cavitation, may be characteristically visualized. Thereby, the spatiotemporal characteristics of the secondary ultrasound signal emitted due to the cavitation, which is important for the therapeutic effect of ultrasound, can be observed clinically.

BRIEF DESCRIPTION OF THE DRAWINGS

FIG. 1 shows an example of a system for realizing a method for displaying a passive cavitation image according to an embodiment of the present invention.

FIG. 2 shows RF signal data of an ultrasound signal received by an imaging probe having a linear array of 64 channels when one bubble is ruptured and a passive cavitation image reconstructed by a DAS beam forming method.

FIG. 3 shows an experimental apparatus that is configured to obtain a passive cavitation image of visualizing an ultrasound distribution induced by the rupture of a bubble generated by focused ultrasound, and an ultrasound B-mode image of bubbles that are obtained by using ultrasound signal thereby.

FIG. 4 shows a portion of an ultrasound RF data received from an imaging probe (20) of the experimental apparatus of FIG. 3.

FIG. 5 shows the result of reconstructing the passive cavitation image by applying ultrasound RF data induced when one bubble representing an arc shape is ruptured.

FIG. 6 (a) shows a passive cavitation image reconstructed by applying DAS beam forming to RF data collected for all times shown in FIG. 4 and FIG. 6 (b) shows an image that is obtained by superimposing the image of FIG. 6 (a) on the B-mode image.

FIG. 7 shows a graph showing the maximum values of ultrasound signals of each frame on all time frames of the passive cavitation image reconstructed by DAS beam forming method on the time axis.

FIG. 8 shows an image of reconstructing a location region and a size of the maximum valve of the image in the time frame in which the bubble rupture occurs as shown in FIG. 7 using the image of FIG. 6.

FIG. 9 sequentially shows the steps of the method for displaying a passive cavitation image according to an embodiment of the present invention.

DETAILED DESCRIPTION OF THE EMBODIMENTS

An embodiment of the present invention will be described with reference to the accompanying drawing hereinafter.

The present invention relates to a method for displaying an ultrasound cavitation image that visualizes the location, the intensity, the time, etc., of the inertial rupture of bubbles by receiving ultrasound generated by an ultrasound cavitation phenomenon.

FIG. 1 shows an example of a system for realizing a method for displaying a passive cavitation image according to an embodiment of the present invention. Referring to FIG. 1, an imaging system 10 generates an ultrasound cavitation image using a signal of an imaging probe 20 that acquires images of a region where the passive cavitation occurs and displays it on a display 30.

The imaging system 10 may be configured to process, operate and store data so as to generate a signal for displaying the passive cavitation image using the signal of the imaging probe 20. For example, the imaging system 10 may include a microprocess, a memory and related hardware and software, and may include a program for performing a method for displaying a passive cavitation image described below. The display 30 may be any display capable of displaying an image, such as a liquid crystal display.

An ultrasound transducer 40 receives pulsed electric power from a pulse power supply 50 to generate ultrasound. For example, the ultrasound transducer 40 may be formed as a piezoelectric element formed of a piezoelectric material such as piezoelectric ceramic. As shown in FIG. 1, the ultrasound transducer 40 may generate a high-pressure, focused ultrasound pulse in the focal region while being submerged in an ultrasound transfer medium 60, thereby bubble group 70 is generated in the ultrasound transfer medium may be formed to cause a passive cavitation phenomenon.

The imaging probe 20 receives ultrasound signal that is generated when the bubbles generated in the focal region are broken and may include a plurality of sensors that are arranged in an array shape for an image generation, i.e., microphones. The imaging probe 20 receives a sound source signal for a localization of a sound source using a microphone array. The imaging probe 20 receives ultrasound signal generated by ruptures of bubbles and generates RF (radio frequency) signal data. The imaging system 10 receives the RF signal data of the imaging probe 20 and processes the received signal to visualize by extracting information on generation location, time, an intensity of rupture signal, etc.

FIG. 2 (a) illustrates typical RF signal data generated by a computer simulation of ultrasound signal received by the imaging probe 20 having a linear array of 64-channel when one bubble is ruptured. The ultrasound signals generated by the cavitation phenomenon are continuously received along a time axis without distance information by the 64 ultrasound transducers. In order to obtain a passive cavitation image, an image signal is synthesized by locating the sound source by time-compensating the distance difference from an image pixel to the receiving element. This method is a known DAS (Delay And Sum) beam forming method, and MATLAB can be used to implement this method. FIG. 2 (b) shows an image obtained by calculating RF signals of the cavitation phenomenon of one bubble by DAS beam forming method. It can be noted that the size distribution of the ultrasound generated by cavitation phenomenon appears as a large signal in a main lobe in a small region in the passive cavitation image, but the signal that is not sufficiently focused neighboring the image pixel is widely distributed around the main lobe as a side lobe.

FIG. 3 (a) shows an experimental apparatus that is configured to obtain a passive cavitation image imaging ultrasound distribution induced by the ruptures of the bubbles generated by a focused ultrasound. The ultrasound transducer 40 for generating focused ultrasound may be fixed to a wall of a tank storing an ultrasound transmitting medium, and the imaging probe 20 of 64-channel linear array for receiving ultrasound signal is disposed at a distance of 32 mm to be perpendicular to an axial direction of the ultrasound transducer 40. FIG. 3 (b) shows ultrasound B-mode image of a bubble group generated by a focused ultrasound within water that is an ultrasound transmitting medium, and at this time the size of the B-mode image is 60 mm*38.4 mm. It was observed that the bubbles generated in the focal region by the focused ultrasound gradually grow over time and then at a certain point inertially contract at a rapid speed to be ruptured, and it is also confirmed that a secondary ultrasound or shock wave is emitted by dynamic behaviors of the bubbles accompanied during this process.

FIG. 4 shows a portion of an ultrasound RF data received from 64 channels of the imaging probe 40 of the experimental apparatus of FIG. 3, and the ultrasound RF data is continuously received and recorded with respect to time without the location information. The ultrasound signal generated by the rupture of the bubbles has a short pulse shape and an arc shaped time delay occurs in all receiving channels. By calculating the magnitude of signal obtained by applying a corresponding focused time delay to an image pixel in a data channel received at a desired time for image acquisition and beam forming, the passive cavitation image can be reconstructed using the RF data of FIG. 4.

FIG. 5 shows a result of reconstructing the passive cavitation image by applying the ultrasound RF data that is generated when one bubble having an arc shape is ruptured. The size of the image was limited to an area of 30 mm*40 mm with a focal depth of 30 mm, and the brightness of the image was displayed using a jet color map in MATLAB. FIG. 5 (a) shows the RF data receiving the ultrasound generated when one bubble is ruptured, and FIG. 5 (b) shows an image that is obtained by reconstructing the same using the DAS beam forming method. The image of FIG. 5 (b) includes complicated side lobes around the position of the bubbles, and an analysis using this image is difficult due to this. If the size information is displayed in a location region that has the maximum brightness in the image as shown in FIG. 5 (c), the side lobe of the passive cavitation image can be removed and at the same time the characteristic information about the main lobe can be clearly displayed.

Since the generation and the rupture of bubbles are dynamic phenomenon, the passive cavitation image changes with time. FIG. 6 (a) shows a passive cavitation image reconstructed by applying DAS beam forming to RF data collected for all times shown in FIG. 4 and FIG. 6 (b) shows an image that is obtained by superimposing the image of FIG. 6 (a) on the B-mode image.

As exemplarily shown in FIG. 5 (b), in the passive cavitation image for the bubble group, the signal of the side lobe appears long vertically around a bright area at the location where the cavitation occurs. Since the side lobe signals appear widely around the main lobe that has a large signal representing the cavitation, the small main lobes representing the cavitation of the small intensity are obscured so that the distribution and the magnitude of the cavitation of the bubble group cannot be clearly observed. Also, when the ultrasound cavitation occurs in the passive cavitation image, while the large signal in the main lobe is maintained for a short time, even a small signal in the side lobe appears in a wide area and is observed for a long time. By superimposing all passive cavitation images over time, the size and the location of all passive cavitation images that occurred can be visualized. However, when the passive cavitation images of all frames are superimposed, the main lobe that is most important information in the cavitation is not clearly distinguished because of the side lobe signal.

According to an embodiment of the present invention, based on the recognition that the ultrasound above a certain intensity generates bubbles and secondary ultrasound or shock wave is generated as a result of dynamic behaviors of the generated bubbles, a passive cavitation image that visualizes the magnitude of the ultrasound emitted by the dynamic behavior of the bubbles in a time-reflected space, focusing on the fact that the time, location and size of the cavitation in the passive cavitation image are key information in order to observe the cavitation over time.

Since the ultrasound signal implemented in the passive cavitation image appears in the form of a pulse having a large signal for a short time when the bubble rupture phenomenon that is important for the biological effect of ultrasound occurs, in an embodiment of the present invention, the maximum value of each time frame is extracted from the passive cavitation image of all time frames and the change of the maximum values are then plotted on the time axis in order to observe the bubble rupture phenomenon.

FIG. 7 shows a graph showing the maximum values of ultrasound signals of each frame on all time frames of the passive cavitation image reconstructed by DAS beam forming method on the time axis, and the lower portion of FIG. 7 shows a time when the pulse-like peak appears. It can be estimated that the bubble ruptures at a time when the graph appears in the form of an impulse.

The signal shown in FIG. 7 is similar to a signal received by a passive cavitation detector, but there is difference therebetween in content. The signal recorded using the passive cavitation detector is obtained by selectively receiving the ultrasound signal emitted by the rupture of the bubbles at a focal point of the passive cavitation detector, but the signal shown in FIG. 7 shows the magnitude of the ultrasound signal emitted by the rupture of the most powerful bubble at each moment. Since the rupture of the most powerful bubble at each moment has a high probability of occurring near the focal point, if only the magnitude of the signal in the focal point in the passive cavitation image over the entire time is represented on the time axis, it is almost the same with the signal of the passive cavitation detector. In this case, the difference between the two signals is affected by the difference in the receiving sensitivity and the frequency characteristics of the sensor of the passive cavitation detector and the sensor of the imaging probe used for realizing the passive cavitation image.

As exemplarily shown in FIG. 5, in the case of a single bubble, in the passive cavitation image reconstructed by applying DAS beam forming, the main lobe signal appears as a point-shaped image and the side lobe signal appears in the surrounding area thereof. The side lobe signal acts as a virtual image and does not give an aid to the analysis of the cavitation, and the main lobe signal has a maximum value in the image of a specific time frame.

The image is reconstructed by the magnitude and position information of the image point at a time when the main lobe signal has a maximum value in the passive cavitation image, and thereby the passive cavitation image in which the influence of the side lobe is removed can be obtained. As shown in FIG. 5 (b), the brightest image point in the image obtained by the DAS beam forming is the position of the main lobe generated by the cavitation signal. In an embodiment of the present invention, by using a method of displaying the magnitude information in a location area having the maximum brightness in the image as exemplarily shown in FIG. 5 (c), the side lobe of the passive cavitation image can be removed and at the same time the characteristic information of the main lobe, e.g., the magnitude, the position and the time can be displayed.

FIG. 8 shows an image of reconstructing a location region and a size of the maximum valve of the image in the time frame in which the bubble rupture occurs as shown in FIG. 7 using the image of FIG. 6. FIG. 8 (a) shows that the maximum brightness is extracted in every time frame when the passive cavitation occurs and it is superimposed at every time frame to be displayed on the B-mode image that is the background image, and it can be seen that the side lobe is removed and the passive cavitation of a small magnitude is well displayed. Further, FIG. 8 (b) shows an image that is obtained by reconstructing the position and the time of the occurrence of the cavitation and displaying the same on the B-mode image. The background image is an image of an area where the passive cavitation occurs, and it may be not only the B-mode image but also an M-mode image, a 3D image, a compounding image or the like. The color in FIG. 8 (a) indicates the magnitude of the signal and the color in FIG. 8 (b) indicates the time of the occurrence.

FIG. 9 sequentially shows the steps of the method for displaying a passive cavitation image according to an embodiment of the present invention. Referring to FIG. 9, an ultrasound signal (RF data) for a passive cavitation is first received using the imaging probe 20 (refer to FIG. 9 (a)), and a first passive cavitation image for the cavitation is generated by a DAS beam forming method using the received RF data in the predetermined respective time frame (refer to FIG. 9 (*b*)). Then, by selecting a main lobe region having a signal magnitude greater than or equal to a predetermined value in the first cavitation image for each time frame and removing signals of the remaining side lobe region, a second passive cavitation image in which a maximum signal region is displayed is generated (refer to FIG. 9 (*c*)). In this case, the main lobe region having the maximum magnitude may be selected as a region having a signal magnitude greater than or equal to a predetermined value. In this case, the second passive cavitation image may include information on the signal magnitude of the maximum signal region, and the information on the signal magnitude may be expressed as a color or gray scale image. In addition, the second passive cavitation image may include information on a signal generation time of the maximum magnitude signal region, and the information on the signal generation time may be expressed as a color or gray scale image. Subsequently, a main lobe passive cavitation image is generated by superimposing the second cavitation image in which the signal region of the maximum magnitude obtained for the respective time frame is displayed (refer to FIG. 9 (*d*)), and a final passive cavitation image is generated by displaying the generated main lobe image on a background image (here, B-mode image) (refer to FIG. 9 (*e*)).

As described above, according to an embodiment of the present invention, a complex side lobe is removed from the passive cavitation image that is obtained by spatiotemporal imaging of the intensity of the ultrasound signal emitted by the cavitation phenomenon, and the location, time and the intensity of the rupture, which are key information of the ultrasound cavitation, may be characteristically visualized. Thereby, the spatiotemporal characteristics of the secondary ultrasound signal emitted due to the cavitation, which is important for the therapeutic effect of ultrasound, can be observed clinically.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

INDUSTRIAL APPLICABILITY

The present invention relates to a method and a device for displaying images, so it has an industrial applicability.

The invention claimed is:

1. A method for displaying a passive cavitation image that shows characteristic information of a passive cavitation, comprising:
    receiving an ultrasound signal caused by the passive cavitation;
    generating a plurality of first passive cavitation images for the passive cavitation at a predetermined respective time frame using the received ultrasound signal by a DAS (Delay And Sum) beam forming;
    generating a plurality of second passive cavitation images in which a maximum magnitude signal region is displayed by selecting a main lobe region having a magnitude greater than or equal to a predetermined value in respective first passive cavitation images;
    generating a main lobe passive cavitation image in which a main region is displayed in the respective time frame by superimposing the plurality of the second passive cavitation images obtained for the respective time frame; and
    generating a passive cavitation image by displaying the main lobe passive cavitation image on a background image.

2. The method of claim 1, wherein the second passive cavitation image comprises information on a signal magnitude of the maximum magnitude signal region.

3. The method of claim 2, wherein the information on the signal magnitude of the maximum magnitude signal region is expressed as a color or gray scale image.

4. The method of claim 1, wherein the second passive cavitation image comprises information on a signal generation time of the maximum magnitude signal region.

5. The method of claim 4, wherein the information on the signal generation time of the maximum magnitude signal region is expressed as a color or gray scale image.

6. The method of claim 1, wherein the second passive cavitation image comprises image information on a signal magnitude of the maximum magnitude signal region shown on a time axis as signal generation time information of the maximum magnitude signal region.

7. The method of claim 6, wherein the information on the signal magnitude of the maximum magnitude signal region is expressed as a color or gray scale image.

8. A device for displaying a passive cavitation image that shows characteristic information of a passive cavitation, comprising:
    an ultrasound transducer that is configured to be able to generate ultrasound to a ultrasound transmitting medium;
    a pulser power supply that generates a pulse power applied to the ultrasound transducer;
    an imaging probe that receives an ultrasound signal caused by a passive cavitation generated by the ultrasound generated in the ultrasound transmitting medium; and
    an imaging system that displays the passive cavitation image using the ultrasound signal received by the imaging probe,
    wherein the imaging system is configured to perform:
    receiving the ultrasound signal caused by the passive cavitation;
    generating a plurality of first passive cavitation images for the passive cavitation at a predetermined respective time frame using the received ultrasound signal by a DAS (Delay And Sum) beam forming;
    generating a plurality of second passive cavitation images in which a maximum magnitude signal region is displayed by selecting a main lobe region having a magnitude greater than or equal to a predetermined value in respective first passive cavitation images;
    generating a main lobe passive cavitation image in which a main region is displayed in the respective time frame by superimposing the plurality of the second passive cavitation images obtained for the respective time frame; and
    generating a passive cavitation image by displaying the main lobe passive cavitation image on a background image.

9. The device of claim 8, wherein the second passive cavitation image comprises information on a signal magnitude of the maximum magnitude signal region.

10. The device of claim 9, wherein the information on the signal magnitude of the maximum magnitude signal region is expressed as a color or gray scale image.

11. The device of claim 8, wherein the second passive cavitation image comprises information on a signal generation time of the maximum magnitude signal region.

12. The device of claim 11, wherein the information on the signal generation time of the maximum magnitude signal region is expressed as a color or gray scale image.

13. The device of claim 8, wherein the second passive cavitation image comprises image information on a signal magnitude of the maximum magnitude signal region shown on a time axis as a signal generation time information of the maximum magnitude signal region.

14. The device of claim 13, wherein the information on the signal magnitude of the maximum magnitude signal region is expressed as a color or gray scale image.

* * * * *